(12) United States Patent
Tan

(10) Patent No.: US 9,504,766 B2
(45) Date of Patent: Nov. 29, 2016

(54) AIR MOVER

(71) Applicant: Foshan Naibao Electric Co., Ltd., Foshan, Guangdong (CN)

(72) Inventor: Lifen Tan, Foshan (CN)

(73) Assignee: Foshan Naibao Electric Co., Ltd. (CN)

(*) Notice: Subject to any disclaimer, the term of this patent is extended or adjusted under 35 U.S.C. 154(b) by 0 days.

(21) Appl. No.: 14/636,888

(22) Filed: Mar. 3, 2015

(65) Prior Publication Data

US 2016/0175472 A1     Jun. 23, 2016

(30) Foreign Application Priority Data

Dec. 22, 2014   (CN) .................... 2014 2 0832692 U

(51) Int. Cl.
| | | |
|---|---|---|
| *A61L 9/00* | (2006.01) | |
| *A62B 7/08* | (2006.01) | |
| *B67D 5/08* | (2006.01) | |
| *A61L 9/12* | (2006.01) | |
| *A61L 9/04* | (2006.01) | |

(52) U.S. Cl.
CPC . *A61L 9/122* (2013.01); *A61L 9/04* (2013.01)

(58) Field of Classification Search
CPC ............. A61L 9/14; B05B 12/02; B05B 3/02
USPC ................ 422/5, 119, 123, 124; 239/71, 69; 43/334, 457
See application file for complete search history.

(56) References Cited

U.S. PATENT DOCUMENTS

2012/0018530 A1* 1/2012 Blaylock ................ A61L 9/122
                                                          239/7

FOREIGN PATENT DOCUMENTS

| CN | 2052076 U | 1/1990 |
|---|---|---|
| CN | 203420945 U | 2/2014 |
| FR | 2250077 A1 | 5/1975 |
| KR | 200183835 Y1 | 6/2000 |
| KR | 20060026937 A | 3/2006 |

OTHER PUBLICATIONS

International Search Report and Written Opinion for Application No. PCT/CN2015/073186 dated Sep. 21, 2015.

* cited by examiner

*Primary Examiner* — Monzer R Chorbaji
(74) *Attorney, Agent, or Firm* — Lerner, David, Littenberg, Krumholz & Mentlik, LLP

(57) ABSTRACT

A blower featuring a hollow casing, a centrifugal fan, a fragrance cartridge, and an air intake grille. The casing has an air inlet and outlet. The centrifugal fan is housed within the casing and contains a rotational motor and a impeller. The impeller is coupled to a motor axle. The air intake grille is housed at the air inlet and can provide a housing for the fragrance cartridge. The fragrance cartridge is removable and can be fixed to the grille by inserting it into the impeller along the axial plane. The blower is easy to use and is able to diffuse fragrances quickly, creating a fragrant atmosphere while promoting air flow.

20 Claims, 3 Drawing Sheets

AIR MOVER

CROSS REFERENCE TO RELATED APPLICATION

The present application claims priority from China Patent Application No. 201420832692.1 filed Dec. 22, 2014, the disclosure of which is hereby incorporated by reference.

BACKGROUND OF THE INVENTION

The present invention relates to an air mover. Today, many public spaces make use of air blowers to improve air circulation, blow-dry wet surfaces, and the like. Blowers can also be used to eliminate odors in the air and create a fragrant atmosphere. Stationary air fresheners are often used in public spaces in order to release fragrances into the surrounding area. However, because air generally circulates slowly, the effect of such air fresheners is not always noticeable. Further, the fragrance tends to linger in one area creating an overpowering concentration of the scent. Therefore, a need exists for an improved blower with the ability to effectively diffuse fragrances.

BRIEF SUMMARY OF THE INVENTION

A portable blower according to one aspect of the disclosure can include a casing, centrifugal fan, fragrance cartridge and air intake grille. The casing may have an air inlet and outlet. The fan can be a centrifugal fan housed within the casing and may contain a rotational motor with a impeller fixed to the motor's axle. The air intake grille may be coupled to the air inlet. The fragrance cartridge is preferably removable and can be fixed atop the grille by inserting it into the impeller along the axial plane.

In one embodiment, the air intake grille contains an insert channel that extends into the casing. The insert channel can have a plurality of internal vents. The fragrance cartridge may be removably installed in the insert channel.

In one embodiment according to the disclosure, the insert channel contains a primary screw thread and the fragrance cartridge has a secondary screw thread complementary with the primary screw thread to form a threaded connection between the insert channel and fragrance cartridge. The primary screw thread may be located on the inner base of the insert channel, and the secondary screw thread may be located on the base of the fragrance cartridge.

One aspect of the disclosure describes an air intake grille which may contain a number of external air vents about the insert channel. A portable blower can contain an air dispersal grille located at the air outlet. The air dispersal grille can have one or more primary and secondary vertical guide vanes. The primary guide vanes can be located on a first side of the air outlet, and the secondary guide vanes can be located on a second lateral side of the air outlet. The primary and secondary guide vanes can be angled towards each other, with their axes forming an inverted 'V'. The angle between the air outlet's central R-line and each of the primary and secondary guide vanes is preferably between about 20° and 30°. The angle between the primary guide vane and the air outlet's central R-line may be different than the angle between the secondary guide vane and the air outlet's central R-line.

Another aspect of the disclosure describes a impeller which may contain a connecting frame on its inner midsection. The motor can be inserted into the impeller and the motor's axle attached to the impeller's connecting frame.

The air outlet can be located at the base of the casing. The top of the casing may have a handle. The fragrance cartridge can have numerous air vents on any of its surfaces.

BRIEF DESCRIPTION OF THE DRAWINGS

A more complete appreciation of the subject matter of the present invention and the various advantages thereof can be realized by reference to the following detailed description, in which reference is made to the accompanying drawings.

DETAILED DESCRIPTION

Figure 1:
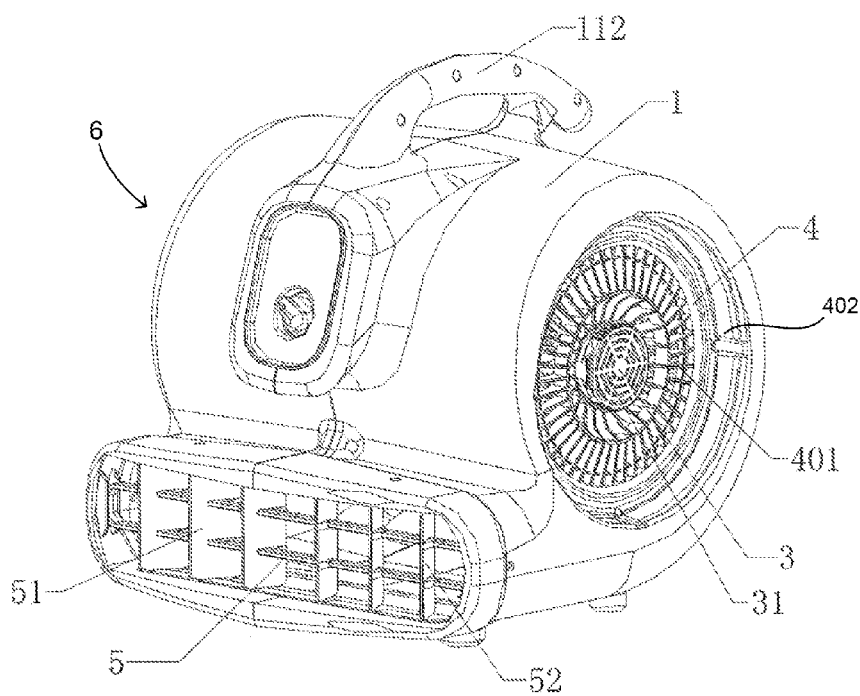
FIG. 1 is a perspective view of a blower in accordance with one embodiment of the current invention.

The present invention relates to components and methods of dispersing fragrant air with a blower. A blower for use with the present invention could be manufactured according to the description provided below or could be adapted from an existing blower accordingly. One example of a blower which could be adapted for use is described in U.S. Patent Publication No. 2012/0141264, the disclosure of which is hereby incorporated by reference herein.

In the embodiment shown in FIGS. 1-6, a portable blower (6) includes a hollow casing (1), a centrifugal fan (2), and an air intake grille (4). The casing (1) contains an air inlet and outlet (101). The centrifugal fan (2) is housed within the casing (1), preferably at or near the inlet, and includes a rotational motor (21) and impeller (22). The impeller shown has a cylindrical shape with a central opening extending the length of the impeller. The impeller could also have any other shape or a solid center. The impeller (22) is fixed to the motor's (21) axle. The air intake grille (4) is positioned at or within the air inlet. The fragrance cartridge (3) is coupled to the air intake grille (4) by inserting the cartridge (3) into the central opening of the impeller (22) along the axial plane. It is believed that positioning the fragrance cartridge (3) within the impeller ensures that the cartridge does not come into contact with any moving parts of blower (6) during use. As will be explained further below, the position of the fragrance cartridge (3) facilitates easy installation and removal of the cartridge. The fragrance cartridge is removable to allow a user to change the cartridge as desired. It is believed that the proximity of the fragrance cartridge (3) to the impeller increases the scent diffusion by providing a greater flow of air over the fragrance cartridge. It is also believed that utilizing the space within the impeller (22) for placement of the fragrance cartridge (3) helps to minimize the size of the blower (6).

As shown, the fragrance cartridge (3) casing has numerous air vents (31) extending through its surfaces which can allow air to flow completely through the cartridge. Of course, the size and spacing of the air vents (31) could have any desired configuration to increase or decrease the flow rate of air through the cartridge. Further, the vents could be on all sides of the cartridge or limited to less than all sides.

In the embodiment shown, the air intake grille (4) contains an insert channel (41) that stands proud of the grille face (402) and extends into the casing (1) when the blower (6) is assembled. The insert channel (41) forms a housing for the fragrance cartridge (3). The external size and shape of the fragrance cartridge (3) is similar to the internal size and shape of the air insert channel (41) such that the cartridge is securely retained within the insert channel (41). The insert channel (41) has a number of internal vents (411). Similarly to the air vents (31) of the fragrance cartridge (3), it is believed that internal vents (411) formed in the insert channel (41) allow air to flow more easily through the fragrance cartridge.

Figure 4:
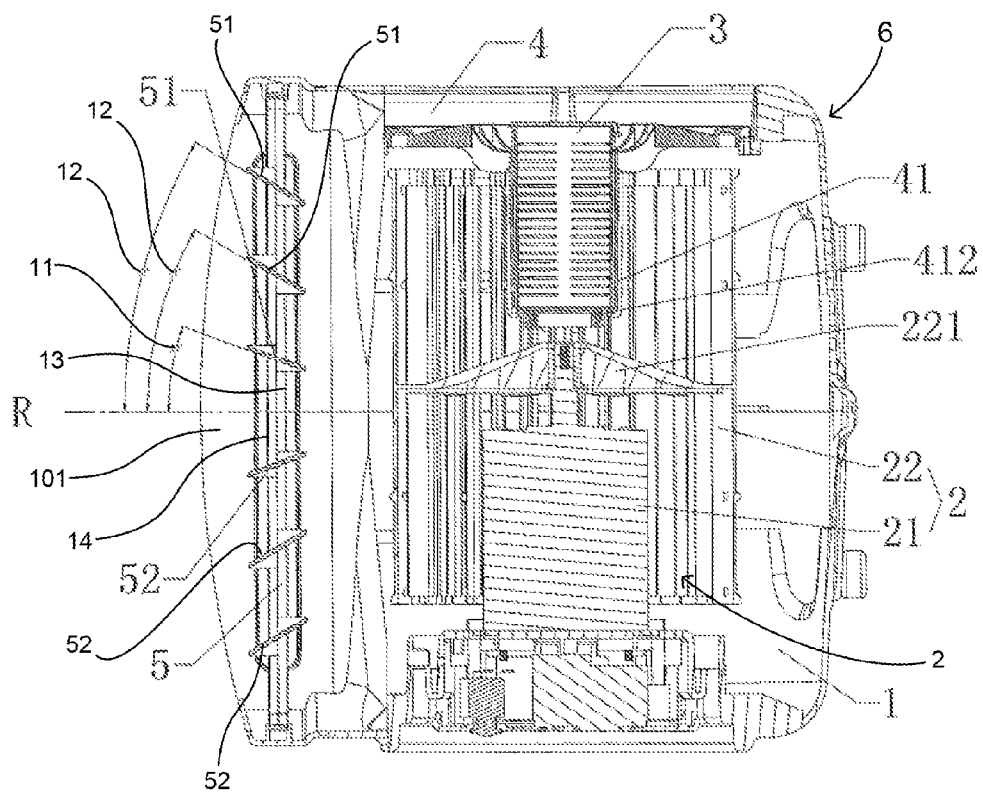
FIG. 4 illustrates a sectional view of the blower along line A-A of FIG. 3.
Figure 5:
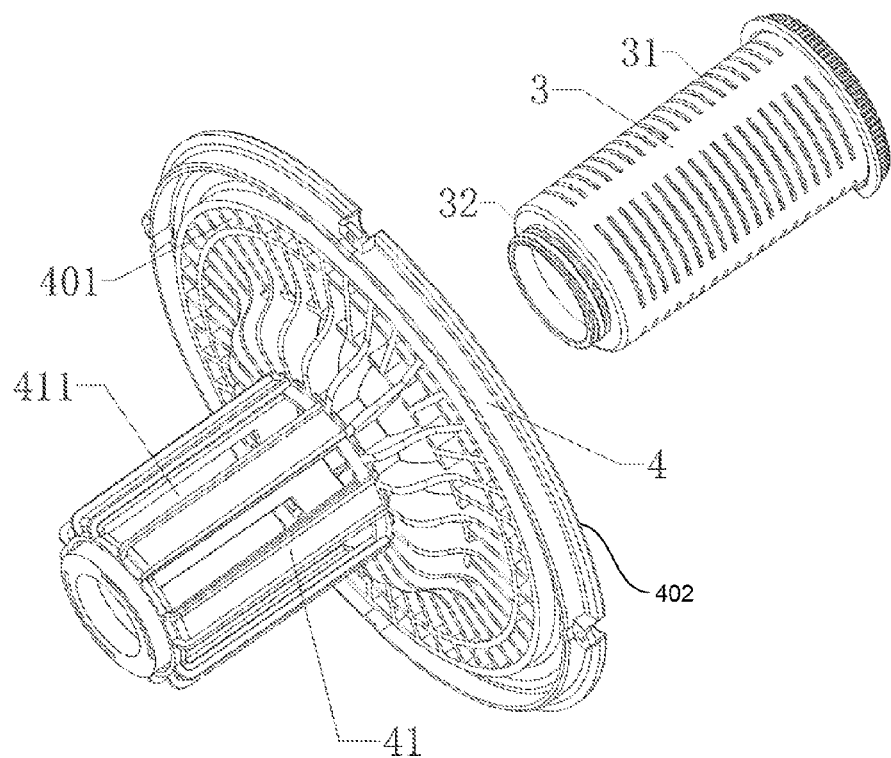
FIG. 5 illustrates a perspective view of one embodiment of an air intake grille and a fragrance cartridge in accordance with one embodiment of the current invention.
Figure 6:
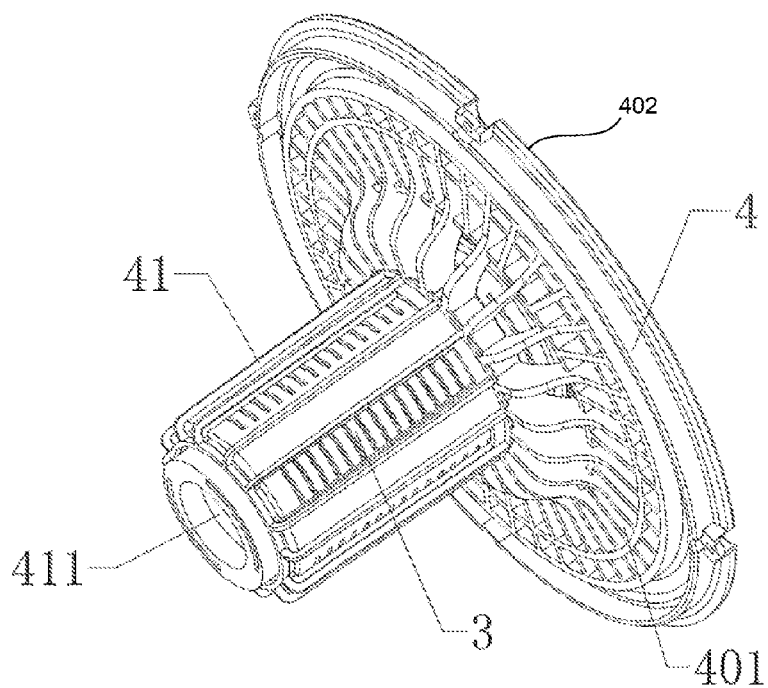
FIG. 6 illustrates a perspective view of the air intake grille of FIG. 5 with the fragrance cartridge coupled to the air intake grille.

The insert channel (41) shown in FIG. 4 contains a primary screw thread (412). The outer wall of the fragrance cartridge (3) has a secondary screw thread (32) which corresponds with the aforementioned primary screw thread (412). The primary and secondary screw threads form a threaded connection between the fragrance cartridge (3) and the insert channel (41). The threaded connection provides at least temporary securement of the cartridge within the channel while also allowing for removal and or replacement of the cartridge when desired. Alternative forms of securing the cartridge in the channel include ball and detent, bayonet locking, and the like.

The primary screw thread (412) is located on the inner base of the insert channel (41), and the secondary screw thread (32) is located on the base of the fragrance cartridge (3). The primary screw thread (412) could also be positioned at any point along the insert channel (41) provided that the secondary screw thread (32) is positioned accordingly to allow the cartridge to be inserted into the channel to the desired depth.

In the embodiment shown, the air intake grille (4) contains a number of external air vents (401) extending through the grille face (402). The external air vents (401) are positioned about the insert channel (41). It is believed that the external air vents (401) promote an even air flow through the fragrance cartridge (3) in cooperation with air vents (31) and internal vents (411).

Figure 2:
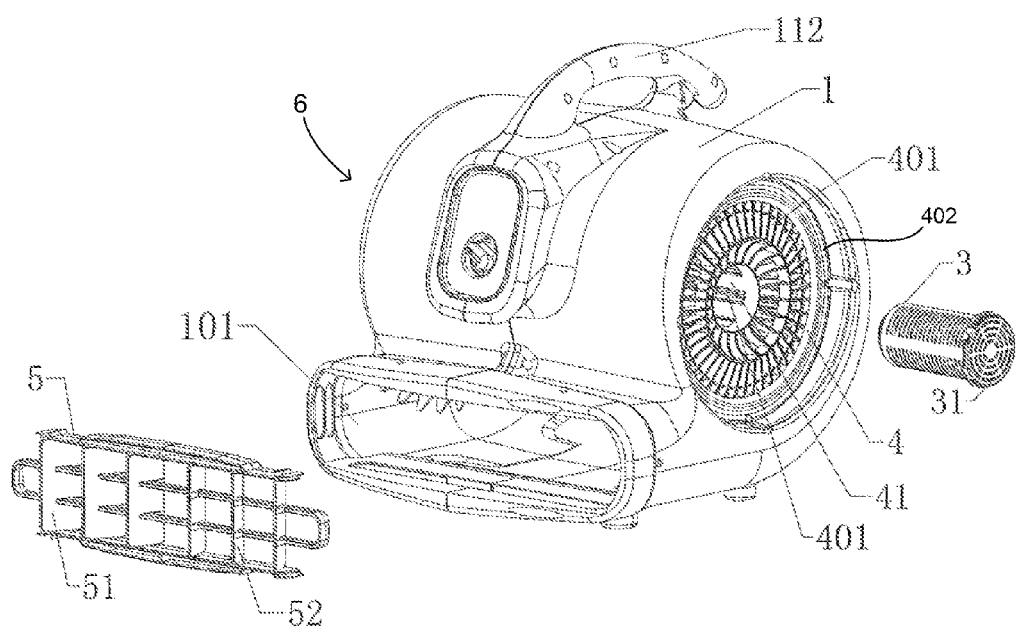
FIG. 2 illustrates a partially exploded view of the blower of FIG. 1.
Figure 3:
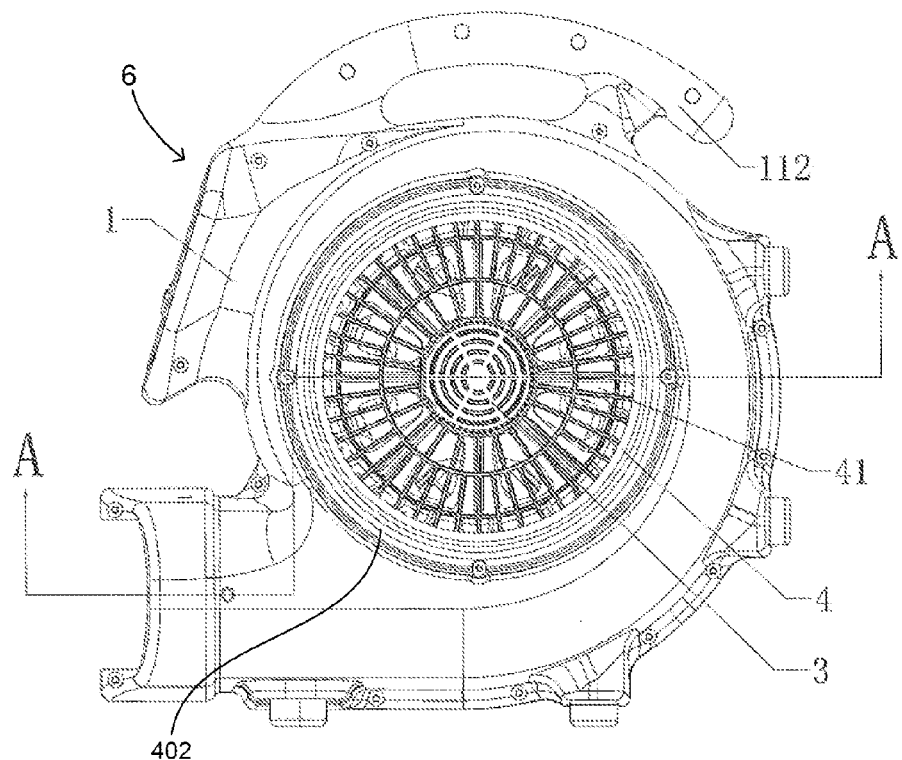
FIG. 3 illustrates a profile view of the blower of FIG. 1.

As best seen in FIGS. 1-2, there is an air dispersal grille (5) located at the air outlet (101). The air dispersal grille (5) has several primary (51) and secondary (52) vertical guide vanes. The primary guide vanes (51) are located on a first lateral side (13), with the secondary guide vanes (52) located on a second lateral side (14). The primary (51) and secondary (52) guide vanes are angled towards each other with their axes forming an inverted 'V' (best seen in FIG. 4). The range of air dispersal may be increased as a result of the blowing angle created by the angled vanes. The angle between the central R-line and each of the primary (51) and secondary (52) guide vanes is between 10° and 50° and preferably between 20° and 30°.

The air dispersal grille (5) shown has three primary (51) and three secondary (52) guide vanes. Of course, the grill could have any number of primary and secondary guide vanes. The angle 12 between the two primary vanes (51) furthest from the central R-line and the central R-line is between about 20° and 40° and preferably about 30°. The angle 11 between the remaining primary guide vane (51) on the first lateral side (13) and the central R-line is between about 10° and 30° and preferably about 20°. For the three secondary guide vanes (52) on the second lateral side (14) of the opening (101), the angle between the central R-line and the two vanes (52) furthest from the central R-line is about between about 20° and 40° and preferably about 30°. The angle between the remaining secondary guide vane (52) on the second lateral side (14) and the central R-line is between about 10° and 30° and preferably about 20°. The primary and secondary vanes could also all form the same angle with the central R-line or each be arranged at different angles.

The impeller (22) contains a connecting frame (221) on its inner midsection which couples the impeller to the motor. The motor (21) inserts into the central opening of the impeller (22) and the motor axle fits securely into the impeller's (22) connecting frame (221). The motor (21) is housed within the impeller (22) to help further reduce the size of the appliance. The connecting frame (221) transfers rotary motion from the motor axle to the impeller. Movement of the impeller creates a flow of air. The impeller pulls air through the air intake grille (4) internal vents (411), and air vents (31). The impeller then expels air through the air dispersal grille (5) and out the outlet (101).

In one embodiment, the casing's (1) air outlet (101) is located at the base of the casing (1). It is believed that this leads to better lower air flow, improving air circulation and enabling faster drying of floors. The casing (1) may include a handle at the top which a user can grasp to move the blower (6). The handle may be formed integrally with the casing or may be a separate piece which is attached to the casing.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A portable blower comprising:
a casing having an air inlet and an air outlet;
a fan within the casing and having a motor and an impeller fixed to the motor, the impeller having an opening therein;
a fragrance cartridge arranged within the opening of the impeller; and
an air intake grille coupled to the air inlet.

2. The portable blower of claim 1, wherein the air intake grille includes an insert channel that extends into the casing.

3. The portable blower of claim 2, wherein the insert channel has a plurality of internal vents.

4. The portable blower of claim 2, wherein the fragrance cartridge is configured to be removable and adapted to be placed within the insert channel.

5. The portable blower of claim 2, wherein the fragrance cartridge is configured to form a threaded connection with the insert channel.

6. The portable blower of claim 5, wherein the threaded connection between the fragrance cartridge and the insert channel is located at an inner base of the insert channel.

7. The portable blower of claim 2, wherein the air intake grille includes a plurality of external air vents about the insert channel.

8. The portable blower of claim 1, further comprising an air dispersal grille at the air outlet.

9. The portable blower of claim 8, wherein the air dispersal grille has at least one primary guide vane located on a first lateral side of the air outlet and at least one secondary guide vane located on a second lateral side of the air outlet.

10. The portable blower of claim 9, wherein the at least one primary guide vane and at least one secondary guide vane are angled towards each other with their axes forming an inverted 'V'.

11. The portable blower of claim 10, wherein an angle between an air outlet's central R-line and each of the at least one primary guide vane and at least one secondary guide vane is between 20 and 30°.

12. The portable blower of claim 11, wherein the angle between the at least one primary guide vane and the air outlet's central R-line is different from the angle between the at least one secondary guide vane and the air outlet's central R-line.

13. The portable blower of claim 10, wherein the angle between the at least one primary guide vane and the air outlet's central R-line is equal to the angle between the at least one secondary guide vane and the air outlet's central R-line.

14. The portable blower of claim 1, wherein the impeller includes a connecting frame on an inner midsection of the impeller.

15. The portable blower of claim 14, wherein the motor has an axle coupled to the connecting frame.

16. The portable blower of claim 1, wherein the air outlet is located at a base of the casing.

17. The portable blower of claim 1, further comprising a plurality of vents formed in the fragrance cartridge.

18. A method of dispersing air comprising:
   obtaining a blower comprising;
   a casing having an air inlet and an air outlet;
   a fan within the casing and having an impeller fixed to the motor, the impeller having an opening therein;
   a fragrance cartridge arranged within the opening of the impeller; and
   an air intake grille coupled to the air inlet;
   placing the blower on a surface; and
   powering the motor to rotate the impeller to create a flow of air.

19. The method of claim 18, further comprising obtaining a replacement fragrance cartridge;
   removing the fragrance cartridge from within the impeller; and
   inserting the replacement fragrance cartridge into the impeller.

20. The method of claim 18, wherein the step of placing the blower on a surface comprises grasping a handle formed at a top of the blower to move the blower to a desired location.

* * * * *